United States Patent
Yamazaki et al.

(10) Patent No.: US 11,639,491 B2
(45) Date of Patent: May 2, 2023

(54) MICROORGANISM LYOPHILIZED COMPOSITION

(71) Applicants: Kumiai Chemical Industry Co., Ltd., Taito-Ku (JP); K.I Chemical Industry Co., Ltd., Iwata (JP); Okayama Prefectural Government, Okayama (JP)

(72) Inventors: Toshinobu Yamazaki, Taito-Ku (JP); Nobutoshi Myojo, Taito-Ku (JP); Shingo Hattori, Iwata (JP); Tatsuya Horiuchi, Iwata (JP); Akira Kawaguchi, Fukuyama (JP); Namiko Kirino, Akaiwa (JP)

(73) Assignees: Kumiai Chemical Industry Co., Ltd., Taito-Ku (JP); K.I Chemical Industry Co., Ltd., Iwata (JP); Okayama Prefectural Government, Okayama (JP)

( * ) Notice: Subject to any disclaimer, the term of this patent is extended or adjusted under 35 U.S.C. 154(b) by 0 days.

(21) Appl. No.: 16/758,947

(22) PCT Filed: Oct. 23, 2018

(86) PCT No.: PCT/JP2018/039398
§ 371 (c)(1),
(2) Date: Apr. 24, 2020

(87) PCT Pub. No.: WO2019/082907
PCT Pub. Date: May 2, 2019

(65) Prior Publication Data
US 2021/0180005 A1    Jun. 17, 2021

(30) Foreign Application Priority Data
Oct. 27, 2017    (JP) .............................. JP2017-208588

(51) Int. Cl.
| | |
|---|---|
| *C12N 1/00* | (2006.01) |
| *C12N 1/04* | (2006.01) |
| *A01N 63/20* | (2020.01) |
| *C12N 1/20* | (2006.01) |
| *A61K 35/74* | (2015.01) |
| *C12R 1/41* | (2006.01) |

(52) U.S. Cl.
CPC ............... *C12N 1/04* (2013.01); *A01N 63/20* (2020.01); *A61K 35/74* (2013.01); *C12N 1/20* (2013.01); *C12N 1/205* (2021.05); *C12R 2001/41* (2021.05)

(58) Field of Classification Search
CPC ....................................................... C12N 1/00
See application file for complete search history.

(56) References Cited

FOREIGN PATENT DOCUMENTS

| | | | |
|---|---|---|---|
| EP | 0 097 459 A1 | 1/1984 | |
| EP | 0203708 A1 * | 12/1986 | .............. C05F 11/08 |
| HU | 191490 * | 6/1986 | |
| JP | 59-2683 A | 1/1984 | |
| JP | 63-63373 A | 3/1988 | |
| JP | 10-243781 A | 9/1998 | |
| WO | WO-2008143782 A1 * | 11/2008 | .............. A61P 31/04 |
| WO | WO 2012/067127 A1 | 5/2012 | |

OTHER PUBLICATIONS

International Search Report dated Dec. 25, 2018 in PCT/JP2018/039398 filed Oct. 23, 2018, 2 Pages.

Akira Kawaguchi, "Studies on Diagnosis and Biological Control of Grapevine Crown Gall and Phylogenetic Analysis of Tumorigenic *Rhizobium vitis*," Bulletin of the Okayama Prefectural Agricultural Experiment Station, vol. 27, 2009, 61 Pages.

Nicholas C. McClure, et al., "Construction of a Range of Derivatives of the Biological Control Strain *Agrobacterium rhizogenes* K84: a Study of Factors Involved in Biological Control of Crown Gall Disease," Applied and Environmental Microbiology, vol. 64, No. 10, Oct. 1998, pp. 3977-3982.

* cited by examiner

*Primary Examiner* — Albert M Navarro
(74) *Attorney, Agent, or Firm* — Obion, McClelland, Maier & Neustadt, L.L.P.

(57) ABSTRACT

Provided herein is a method for producing a lyophilized composition of viable cells of *Rhizobium* bacteria having high viable cell viability, and a lyophilized composition of viable cells of *Rhizobium* bacteria having desirable long-storage survivability, among others. The lyophilized composition of viable cells of *Rhizobium* bacteria having high viable cell viability and desirable long-storage survivability can be obtained when a composition containing viable cells of *Rhizobium* bacteria and more than 10 mass % moisture is lyophilized to bring the moisture content to 10 mass %, and the drying is ended before the moisture content becomes less than 5 mass % so that the composition after the lyophilization contains the viable bacteria and 5 to 10 mass % of moisture.

7 Claims, No Drawings

MICROORGANISM LYOPHILIZED COMPOSITION

TECHNICAL FIELD

The present invention relates to a lyophilized composition of viable bacteria of the genus *Rhizobium*, among others. Specifically, the present invention relates to a lyophilized *Rhizobium* composition containing a high content of viable cells (high viable cell viability), and to a method thereof and use thereof, among others.

BACKGROUND ART

Crown gall disease is a plant disease caused by pathogenic soil bacteria *Rhizobium radiobacter* (other name: *Agrobacterium tumefaciens*), *Rhizobium rhizogenes* (other name: *Agrobacterium rhizogenes*), and *Rhizobium vitis* (other name: *Agrobacterium vitis*) (in the following, there are cases where these may be referred to collectively as "crown gall bacteria"). Tumors called crown gall form on plants infected by these pathogens. The disease develop reducing plant vigor, and, in severe cases, leading to decline and die. In Japan, crown gall disease is developed for the most part in fruits and flowers, thus damaging seriously to farming of fruits and flowers, and in managing of trees in places such as parks.

All of the crown gall-causing bacteria above have the Ti (tumor-inducing) plasmid, which induces tumors when the nuclear DNA of a plant cell is transformed with a part of the Ti-plasmid (T-DNA region). Once a tumor is formed, the tumor keeps growing even in the absence of crown gall bacteria, until it leads the plant to decline and die. Therefore, at present, it is difficult to cure the plants affected by crown gall disease. An important measure for control of crown gall disease, therefore, is to prevent a plant from being infected by crown gall bacteria.

Traditionally, such preventive measures against infection with crown gall bacteria have mostly been implemented by heat sterilization of the entire soil contaminated with crown gall bacteria, soil fumigation with a soil disinfectant such as a chloropicrin agent or a methyl bromide agent, or soil treatment with an antibiotic for Gram-negative bacteria (because of crown gall bacteria being Gram negative). A drawback, however, is that these methods result in creating poor soil by also sterilizing and removing useful soil bacteria in the soil, in addition to the crown gall bacteria. An organic fertilizer needs to be applied or other measures are needed to bring such poor soil back to soil conditions suited for intended plant growth. However, this requires a great deal of time, cost, and labor. The soil disinfectants used in fumigation are very toxic, and pose health risks to workers and people in the neighborhood.

As an alternative approach, control methods that use non-pathogenic bacteria as biopesticides have been proposed. Methods that are considered particularly effective are methods wherein use non-pathogenic *Rhizobium* bacteria as biopesticides. For example, PTL 1 discloses a method that uses the non-pathogenic F2/5 (pT2TFXK) strain of *Rhizobium vitis* (other name: *Agrobacterium vitis*) as an antagonistic bacterium (PTL 1), PTL 2 discloses a control method wherein uses the non-pathogenic ARK-1, ARK-2, and ARK-3 strains of *Rhizobium vitis* as biopesticides, NPL 1 discloses a method wherein uses the non-pathogenic VAR03-1 strain of *Rhizobium vitis* as an antagonistic bacterium, and NPL 2 discloses an antagonistic control method wherein uses the non-pathogenic K84 strain of *Rhizobium rhizogenes* (other name: *Agrobacterium radiobacter*) as a biopesticide.

These *Rhizobium* bacteria can be cultured under aerobic conditions using, for example, liquid culture (e.g., aerated agitation culture, and shaking culture), and solid culture. Of these techniques, liquid culture is more suited for industrial applications, where large quantities of viable bacteria need to be produced in a short amount of time. For example, an aqueous culture solution containing a high concentration of viable *Rhizobium* bacteria can be obtained by culturing *Rhizobium* bacteria by using a liquid medium such as LB (Luria-Bertani) medium.

An aqueous liquiform agrichemical composition using such an aqueous culture solution as raw material is the most convenient form as a biopesticide containing non-pathogenic *Rhizobium* bacteria as an agrichemical active component. However, because *Rhizobium* bacteria are obligately aerobic bacteria, viable cells of *Rhizobium* bacteria continually consume dissolved oxygen in the aqueous liquiform agrichemical composition. An oxygen supply, such as by aeration, is therefore required to maintain survival of viable *Rhizobium* bacteria in an aqueous culture solution. However, for distribution in the form of an agrichemical composition, the aqueous culture solution needs to be charged and sealed in a container such as a bottle, and, once packed, the bacteria have essentially no access to oxygen. That is, an aqueous liquiform agrichemical composition product containing the aqueous culture solution as a main component is not suited for storage, and is not practical in actual applications. A more suitable form of a biopesticide containing viable cells of non-pathogenic *Rhizobium* bacteria as an agrichemical active component would probably be a solid agrichemical composition prepared by solidifying the aqueous culture solution by using some means.

However, an aqueous culture solution using a liquid medium as a main component contains a large amount of moisture, therefore a method that forms a powder by adsorbing the aqueous culture solution to a water absorbent carrier such as silica (white carbon) requires a large amount of water absorbent carrier. As a result, the number of viable cells per unit mass is small in this method. That is, according to this method, the solid agrichemical composition contains only a low concentration of agrichemical active component. Because the control effect of such a solid agrichemical composition depends on the number of active component viable bacteria, the solid agrichemical composition needs to be used in large quantity in actual settings. This poses inconvenience, and the large package size is disadvantageous in terms of delivery and storage.

To circumvent this, solidification of the aqueous culture solution is achieved by a method that dries the culture to remove moisture, and obtains the residue as the solid component. However, viable cells of *Rhizobium* bacteria are weak against exposure to heat, and drying methods such as spray drying are not easily applicable because these methods involve exposure to high temperature. A more potent approach for removal of moisture by drying is lyophilization, which enables nonthermal removal of moisture. In lyophilization, a precooled, frozen hydrous composition is placed under a near-vacuum reduced pressure, and the moisture in the composition is removed by sublimation of water in a frozen state. This technique has been used for a wide range of compositions containing viable cells of microorganisms (PTL 3 to 5, NPL 3).

These prior art techniques have provided a source of reference for production of a lyophilized composition containing viable cells of *Rhizobium* bacteria. However, as it currently stands, lyophilization involves a high percentage reduction of viable cells of *Rhizobium* bacteria, and the technique is insufficient and unsatisfactory as an industrial method of production of an agrichemical composition containing viable cells of *Rhizobium* bacteria. Compositions produced by lyophilization in the manner described above are also not satisfactory in terms of long-term survivability of viable cells of *Rhizobium* bacteria during storage.

Under these circumstances, there is a need in the industry for development of a technique for producing a lyophilized composition of viable cells of *Rhizobium* bacteria having high viable cell viability, and a technique for production and storage of a lyophilized composition of viable cells of *Rhizobium* bacteria having desirable long-storage survivability.

PRIOR ART CITATION LIST

Patent Literature

PTL 1: U.S. Pat. No. 7,141,395
PTL 2: WO2012/67127
PTL 3: JP-T-2005-538939
PTL 4: JP-T-2007-517888
PTL 5: JP-T-2012-525122

Non Patent Literature

NPL 1: Kawaguchi, A., Studies on the diagnosis and biological control of grapevine crown gall and phylogenetic analysis of tumorigenic *Rhizobium vitis*. Journal of General Plant Pathology 75:462-463 (2009)
NPL 2: Nicholas C. McClure et al., Construction of a Range of Derivative of the Biological Control Strain *Agrobacterium rhizogenes* K84: A Study of Factors Involved in Biological Control of Crown Gall Disease. Appl. Environ. Microbiol. 64:3977-3982 (1998)
NPL 3: Tomotari Mitsuoka, A Study of Bifidobacteria, Japan Bifidus Foundation, July 1994, p. 256-259

SUMMARY OF INVENTION

Technical Problem to be Solved by Invention

An object of the present invention is to provide a method for producing a lyophilized composition of viable cells of *Rhizobium* bacteria having high viable cell viability, and a lyophilized composition of viable cells of *Rhizobium* bacteria having desirable long-storage survivability, among others. Another object of the present invention is to provide a method for controlling crown gall disease with an agrichemical composition containing non-pathogenic *Rhizobium* bacteria as an agrichemical active component and that can be efficiently produced by using the foregoing method of production and other techniques, and that can be used in actual crop production, among others.

Means for Solving Problem

The present inventors conducted intensive studies to achieve the foregoing objects, and found that a lyophilized composition of viable cells of *Rhizobium* bacteria having high viable-cell viability and desirable long-storage survivability can be obtained when a composition containing viable cells of *Rhizobium* bacteria and more than 10 mass % moisture is lyophilized to bring the moisture content to 10 mass %, and the drying is ended before the moisture content falls below 5 mass % so that the composition after the lyophilization contains viable cells of the *Rhizobium* bacteria and 5 to 10 mass % moisture. The present invention was completed on the basis of this finding.

Specifically, embodiments of the present invention are as follows.

(1) A lyophilized microbial composition as a lyophilized composition of viable cells of a *Rhizobium* bacterium, the composition comprising 5 to 10 mass % moisture.

(2) The lyophilized composition according to (1), wherein the *Rhizobium* bacterium is one or two or more selected from *Rhizobium radiobacter*, *Rhizobium rhizogenes*, and *Rhizobium vitis*.

(3) The lyophilized composition according to (1) or (2), wherein the *Rhizobium* bacterium is non-pathogenic.

(4) The lyophilized composition according to (3), wherein the *Rhizobium* bacterium is one or two or more selected from *Rhizobium vitis* ARK-1 strain (FERM BP-11426), *Rhizobium vitis* ARK-2 strain (FERM BP-11427), *Rhizobium vitis* ARK-3 strain (FERM BP-11428), and *Agrobacterium radiobacter* K84 strain.

(5) A method for inhibiting decrease of viability of viable cells of a *Rhizobium* bacterium in a lyophilized composition, comprising storing the lyophilized composition of any one of (1) to (4) at 0 to 10° C.

(6) A method for controlling crown gall disease, comprising immersing a seedling, namely young plant, of a useful plant before planting permanently in a suspension prepared as an aqueous dispersion of the lyophilized composition of (3) or (4) and containing viable cells of the non-pathogenic *Rhizobium* bacterium.

(7) A method for controlling crown gall disease, comprising pulverizing the lyophilized composition of (3) or (4), and dressing an unplanted seedling of a useful plant with a powder containing the pulverized composition and viable cells of the non-pathogenic *Rhizobium* bacterium.

(8) A method for producing a lyophilized microbial composition, comprising the step of lyophilizing a composition containing viable cells of a *Rhizobium* bacterium and more than 10 mass % moisture, wherein the lyophilization step is a step that freezes the composition, and then dries the composition under a reduced pressure to bring the moisture content to 10 mass %, and in which the drying is ended before the moisture content falls below 5 mass % so that the composition after the lyophilization contains viable cells of the *Rhizobium* bacterium and 5 to 10 mass % moisture.

(9) The method according to (8), wherein the *Rhizobium* bacterium is one or two or more selected from *Rhizobium radiobacter*, *Rhizobium rhizogenes*, and *Rhizobium vitis*.

(10) The method according to (8) or (9), wherein the *Rhizobium* bacterium is non-pathogenic.

(11) The method according to (10), wherein the *Rhizobium* bacterium is one or two or more selected from *Rhizobium vitis* ARK-1 strain (FERM BP-11426), *Rhizobium vitis* ARK-2 strain (FERN BP-11427), *Rhizobium vitis* ARK-3 strain (FERM BP-11428), and *Agrobacterium radiobacter* K84 strain.

Advantageous Effects of Invention

With the present invention, a lyophilized composition that has reduced loss of viable cells of *Rhizobium* bacteria (high viable-cell viability) can be obtained. A lyophilized composition of viable cells of *Rhizobium* bacteria having desirable long-term preservation stability also can be obtained. The present invention also enables effective control of crown gall disease in applications such as in actual crop production with the use of a biopesticide composition produced by applying non-pathogenic *Rhizobium* bacteria to the present invention.

DESCRIPTION OF EMBODIMENTS

The present invention relates to a lyophilized composition of viable cells of *Rhizobium* bacteria. Examples of the *Rhizobium* bacteria used in the present invention include *Rhizobium alamii, Rhizobium alkalisoli, Rhizobium cellulosilyticum, Rhizobium daejeonense, Rhizobium endophyticum, Rhizobium etli, Rhizobium fabae, Rhizobium gallicum, Rhizobium giardinii, Rhizobium grahamii, Rhizobium hainanense, Rhizobium huautlense, Rhizobium galegae, Rhizobium indica, Rhizobium indicus, Rhizobium indigoferae, Rhizobium larrymoorei, Rhizobium leguminosarum, Rhizobium leucaenae, Rhizobium loessense, Rhizobium lupini, Rhizobium lusitanum, Rhizobium mesosinicum, Rhizobium miluonense, Rhizobium mongolense, Rhizobium multihospitium, Rhizobium nagarjuna nagarensis, Rhizobium oryzae, Rhizobium phaseoli, Rhizobium pisi, Rhizobium pusense, Rhizobium radiobacter, Rhizobium rhizogenes, Rhizobium rubi, Rhizobium selenitireducens, Rhizobium soli, Rhizobium Bullae, Rhizobium tibeticum, Rhizobium trifolii, Rhizobium tropici, Rhizobium tuxtlense, Rhizobium undicola, Rhizobium validum*, and *Rhizobium vitis*. Artificially modified strains of these bacteria (for example, through mutations or genetic recombination) are also usable.

Among the *Rhizobium* bacteria listed above, the present invention is suitably applicable to *Rhizobium radiobacter, Rhizobium rhizogenes*, and *Rhizobium vitis*. The lyophilized composition of the present invention, and the method of production thereof are applicable to both crown gall bacteria and non-pathogenic *Rhizobium* bacteria. However, the *Rhizobium* bacteria need to be non-pathogenic when the intended use is a biopesticide such as for control of crown gall disease. Examples of non-pathogenic *Rhizobium* bacteria for which the present invention is suited include the F2/5 (pT2TFXK) strain of *Rhizobium vitis* (other name: *Agrobacterium vitis*) (see PTL 1), the ARK-1, ARK-2, and ARK-3 strains of *Rhizobium vitis*, and the K84 strain of *Rhizobium rhizogenes* (other name: *Agrobacterium radiobacter*; available from Nihon Nohyaku Co., Ltd. under the trade name Bacterose®). The present invention is also applicable to other naturally occurring non-pathogenic *Rhizobium* bacteria, as well as other non-pathogenic *Rhizobium* bacteria that have been artificially modified through, for example, mutations or genetic recombination. However, the present invention is particularly suited for the non-pathogenic ARK-1, ARK-2, and ARK-3 strains of *Rhizobium vitis*, and the non-pathogenic K84 strain of *Agrobacterium radiobacter*. In the specification, a lyophilized composition of the present invention using non-pathogenic *Rhizobium* bacteria may be referred to as "present agrichemical composition" or, simply, "agrichemical composition".

The non-pathogenic ARK-1, ARK-2, and ARK-3 strains of *Rhizobium* bacteria were first deposited at The National Institute of Advanced Industrial Science and Technology, Patent Organism Depositary (currently, The National Institute of Technology and Evaluation, Patent Organism Depositary) under these names on Oct. 14, 2010 (address: 2-5-8, Kazusa-Kamatari, Kisarazu, Chiba, 292-0818), and were later transferred to an international depositary authority (Oct. 31, 2011) with international deposition numbers FERM BP-11426, FERM BP-11427, and FERM BP-11428, respectively.

In order to provide a material for inoculation of pathogens in, for example, a field experiment, a lyophilized product of the present invention may be used as crown gall bacteria, though, in this case, the lyophilized product may not be applicable as an agrichemical composition. It is also possible to use any *Rhizobium* bacteria to produce the present lyophilized composition for any applications, including storage of viable bacteria.

The *Rhizobium* bacteria used in the present invention can be grown by culturing an isolated inoculum. The inoculum may be obtained by culturing the bacterial strains deposited in depositary authorities such as above, or culturing commercially available strains, using, for example, a plate medium. Alternatively, a skilled person will be able to isolate the desired strain from any of *Rhizobium* strains commonly occurring in nature. For example, foreign strains, and strains that have been mutated in a closed environment are also available from biological resource institutions such as the NITE, abbreviation of The National Institute of Technology and Evaluation, Biotechnology Center (NRBC), provided that the strains are known strains. For inoculation, it is also possible to use non-naturally occurring bacterial strains, for example, such as bacterial strains artificially produced by genetic recombination, which may be strains produced in a laboratory or strains provided by an external source, or may be pure cultures of these strains.

The *Rhizobium* bacteria may be cultured by liquid culture or solid culture for both preculture and main culture. However, liquid culture is more suited for industrial applications, where large quantities of viable bacteria need to be produced in a short amount of time.

Examples of the carbon source of the medium used for liquid culture include sugars such as glucose, sucrose, soluble starch, saccharified starch solution, and molasses, and organic acids such as citric acid. The nitrogen source may be appropriately selected from, for example, ammonia, and ammonium salts and nitrates, such as ammonium sulfate, ammonium phosphate, ammonium chloride, and ammonium nitrate. Examples of the mineral salts include phosphoric acid salts, potassium salts, magnesium salts, and manganese salts, for example, such as potassium dihydrogen phosphate, potassium chloride, calcium chloride, magnesium sulfate, manganese sulfate, and ferrous sulfate. As desired, it is also possible to add trace amounts of organic nutrients such as vitamins, amino acids, and nucleic acid-related substances, and organic materials such as peptone, meat extracts, yeast extracts, and soybean meal. Optionally, various other additives, such as a defoaming agent, also may be added.

Specific examples of medium compositions suited for liquid culture of *Rhizobium* bacteria include a medium containing 0.5 g of yeast extract, 5 g of mannitol, 5 g of lactose, 0.5 g of dipotassium phosphate, 0.2 g of sodium chloride, 0.2 g of calcium chloride dihydrate, 0.1 g of magnesium sulfate heptahydrate, 0.1 g of iron(III) chloride hexahydrate, and 1,000 mL of distilled water, and that has been adjusted to pH 7, and a medium containing 1 g of yeast extract, 10 g of mannitol, 200 mL of soil extract, and 800 mL of distilled water, and that has been adjusted to pH 7.2. It is also possible to use an LB medium (a mixture of 5 g of tryptone, 2.5 g of yeast extract, 5 g of sodium chloride, 0.2 mL of a 5 N sodium hydroxide aqueous solution, and 1,000 mL of distilled water). However, the medium is not limited to these examples, and a person with ordinary skill in the art will be able to design an optimum medium composition according to conditions such as the nutrient requirement characteristics of the bacterial strain of interest. Fed-batch culture is also possible.

All procedures of *Rhizobium* bacteria culture are aseptically performed, including medium preparation. Materials to be used as medium components are sterilized before use. Typically, sterilization may be achieved by steam sterilization using an autoclave. However, appropriately selected alternative means may be used for materials that cannot withstand high temperature and high pressure. Non-limiting examples of sterilization methods other than steam sterilization include heat sterilization such as direct flame sterilization and dry heat sterilization; electromagnetic sterilization that applies ionizing radiation such as y rays, X-rays, and ultraviolet rays (UV-C) of 200 to 280 nm wavelengths, or non-ionizing radiation such as microwaves and high-frequency waves; gas sterilization using, for example, ethylene oxide gas; chemical sterilization that makes use of chemical actions, such as ethanol sterilization, hydrogen peroxide low-temperature plasma sterilization, and sterilization using, for example, glutaraldehyde, phthaldialdehyde, hypochlorous acid, and peracetic acid; and sterilization by means of separation and removal, such as filtration.

*Rhizobium* bacteria are obligately aerobic bacteria, and consume dissolved oxygen in an aqueous culture solution. It is therefore preferable to carry out aeration culture to supplement oxygen. Stirring culture or shaking culture is also preferred in terms of efficient use of medium nutrients by *Rhizobium* bacteria.

The isolated *Rhizobium* bacteria are cultured by inoculating the medium prepared in the manner described above. Preferably, the bacteria are grown first by preculture (expansion culture) with a small quantity of medium until the number of cultured cells reaches the stationary phase in their growth curve, before carrying out main culture with sufficient numbers of precultured cells using a large quantity of medium. The culture temperature is selected from typically about 10 to 40° C., preferably about 15 to 35° C. However, the culture temperature is not particularly limited, and a person with ordinary skill in the art will be able to select an appropriate medium temperature according to the optimum growth temperature of the bacterial strain of interest. The standard culture time is about 24 to 72 hours. However, the culture time also may be appropriately adjusted according to conditions such as growth of the bacterial strain.

The aqueous culture solution after finishing culture may directly be used as a material of a lyophilized composition. However, because the aqueous culture solution contains a large amount of moisture, the lyophilization of the aqueous culture solution requires large electric power. It is therefore highly preferable to remove a certain amount of moisture in the aqueous culture solution before lyophilization, and use the resulting concentrate of viable cells of *Rhizobium* bacteria as a material of a lyophilized composition. The method used to obtain a concentrate of viable cells of *Rhizobium* bacteria from the aqueous culture solution is not particularly limited, as long as it does not damage the viable cells. As an example, the concentrate may be obtained by using a dehydration technique such as centrifugation.

In the case of concentration process by the centrifugation exemplified above can remove most of the moisture in the aqueous culture solution, together with the dissolved medium components, and the dissolved substances produced by the *Rhizobium* bacteria. When it is desired to further reduce the impurities contained in the concentrate of viable cells of *Rhizobium* bacteria, the concentrate may be recentrifuged in the form of a dispersion prepared by dispersing the concentrate in sterile water or the like, and the washing procedure may be repeated until the impurity content in the concentrate falls below the desired level.

In lyophilization of viable cells of microorganism such as *Rhizobium*, it is preferable to add a protecting agent before lyophilization (at the end of culture or after concentration) so that the viable cells can be protected from cell injury due to freezing of the moisture in the cells. Examples of the protecting agent include proteins and hydrolysates thereof, carbohydrates (sugars), sugar alcohols, amino acids and salts thereof, and ionic halide salts. Specific examples of these protecting agents are listed below. However, the protecting agent used in the present invention is not limited to the following examples.

Examples of the proteins include human serum albumin, bovine serum albumin, egg albumin, gelatin, immunoglobulins, soy protein, wheat protein, skim milk, casein, and milk serum protein. It is also possible to use hydrolysates of these proteins.

Examples of the carbohydrates (sugars) include: trioses such as dihydroxyacetone and glyceraldehyde; tetroses such as erythrulose, erythrose, and threose; pentoses such as ribulose, xylulose, ribose, arabinose, xylose, lyxose, and deoxyribose; hexoses such as psicose, fructose, sorbose, tagatose, allose, altrose, glucose, mannose, gulose, idose, galactose, talose, fucose, fuculose, and rhamnose; heptoses such as sedoheptulose and coriose; disaccharides such as sucrose, lactulose, lactose, maltose, trehalose, cellobiose, kojibiose, nigerose, isomaltose, isotrehalose, neotrehalose, sophorose, laminaribiose, gentiobiose, turanose, maltulose, palatinose, gentiobiulose, mannobiose, melibiose, melibiulose, neolactose, galactosucrose, scillabiose, rutinose, vicianose, xylobiose, and primeverose; trisaccharides such as nigerotriose, maltotriose, melezitose, maltotriulose, raffinose, and kestose; tetrasaccharides such as acarbose, nistose, nigerotetraose, and stachyose; oligosaccharides such as maltooligosaccharides, isomaltooligosaccharides, galactooligosaccharides, xylooligosaccharides, gentiooligosaccharides, nigerooligosaccharides, fructooligosaccharides, soybean oligosaccharides, and mannanoligosaccharides; and polysaccharides such as amylose, amylopectin, glycogen, cellulose, chitin, agarose, carrageenan, dextrin, maltodextrin, cyclodextrin, heparin, hyaluronic acid, pectin, xyloglucan, and agar.

Examples of the sugar alcohols include glycerol, erythritol, threitol, arabitol, xylitol, ribitol, iditol, galactitol, sorbitol, mannitol, volemitol, perseitol, inositol, and quercitol.

Examples of the amino acids include alanine, arginine, asparagine, aspartic acid, cysteine, glutamine, glutamic acid, glycine, histidine, isoleucine, leucine, lycine, methionine, phenylalanine, proline, serine, threonine, triptophan, tyrosine, and valine. It is also possible to use salts of these amino acids.

Examples of the ionic halide salts include sodium chloride, magnesium chloride, potassium chloride, calcium chloride, zinc chloride, ammonium chloride, sodium bromide, magnesium bromide, potassium bromide, calcium bromide, zinc bromide, ammonium bromide, sodium iodide, magnesium iodide, potassium iodide, calcium iodide, zinc iodide, and ammonium iodide.

It is also possible to use other protecting agents, examples of which include: salts such as magnesium sulfate and calcium carbonate; alkylamines such as methylamine; betaines such as trimethylglycine; and water-soluble cellulose ethers such as carboxymethyl cellulose. Other examples include propylene glycol, dimethyl sulfoxide, polyethylene glycol, polyvinyl alcohol, polyvinyl pyrrolidone, a polyoxyethylene/polyoxypropylene block copolymer, and surfactants.

Aside from the protecting agent, it is also possible to optionally add other components, including, for example, a pH adjuster such as an acid and a base, a defoaming agent such as a silicone- or polyether-base defoaming agent, and a coloring agent such as a pigment.

The protecting agent and other additional components may be used alone or in any combination of two or more. The protecting agent and other additional components may be dissolved in a small amount of sterile water or the like beforehand, and the resulting protecting agent solution may be directly added and mixed into an aqueous culture solution of viable cells of *Rhizobium* bacteria, or into a concentrate of viable cells. In the specification, an aqueous culture solution of viable cells of *Rhizobium* bacteria, a concentrate thereof, and a composition containing these and a protecting agent may be collectively referred to as "liquid stock of viable cells of *Rhizobium* bacteria" or, simply, "liquid stock of viable bacteria".

For prefreezing, the liquid stock of viable cells of *Rhizobium* bacteria is cooled under ordinary pressure conditions. The prefreezing temperature is not particularly limited, as long as it is below the eutectic point of the liquid stock of viable bacteria. Typically, prefreezing is carried out at a low temperature of about −80 to −20° C. Normally, prefreezing freezes a liquid stock of viable cells of a single specific strain of *Rhizobium* bacteria. It is possible, however, to prefreeze a liquid stock of viable cells of more than one strain of *Rhizobium* bacteria.

After prefreezing, the liquid stock of viable bacteria is dried by removing moisture in a frozen state by sublimation under a reduced pressure of about 1 to 100 Pa. Here, the lyophilization process itself may be carried out using a known method. However, when performed in an ordinary fashion until the moisture content in the viable cell cake falls below 5 mass %, the lyophilization, because of the long drying time, results in producing a lyophilized composition containing much smaller numbers of viable cells of *Rhizobium* bacteria than those contained in the liquid stock of viable bacteria before lyophilization. In the production of the present lyophilized composition, the final lyophilized composition has a remaining moisture content of 5 mass % or more. To this end, the drying needs to be stopped when the liquid stock is considered still wet in the context of ordinary lyophilization. On the other hand, a lyophilized composition with a moisture content of more than 10 mass % shows a level of stickiness that is too serious to be ignored for handling. Such high moisture also has a possibility of causing propagation of unwanted bacteria during storage, and decomposing the lyophilized composition. A moisture content of more than 10 mass % is also undesirable because of its potential adverse effect on long-term survivability of viable cells of *Rhizobium* bacteria during storage of the lyophilized composition. It is therefore required that the drying is ended at a set time point where the viable cell cake has a moisture content of 5 to 10 mass %.

The conventional belief is that a lyophilized composition containing viable cells of microorganisms should have a moisture content of desirably less than 5 mass %, for example, 0.1 to 4.5 mass %, preferably about 3 mass %. A rather surprising finding of the present invention, which is also contradictory to this common belief, is that the viability of viable cells of *Rhizobium* bacteria before and after lyophilization, and the long-term survivability of viable cells in a lyophilized composition are improved by intentionally keeping a moisture content of 5 mass % or more in the lyophilized composition. To our surprise, the end point of drying often falls in the constant drying period where drying takes place in a relatively smooth fashion. It is accordingly required to strictly set the end point because the appropriate range of drying time is narrow when controlling drying intensity by drying time. The end point may be set by, for example, experimentally finding the drying time that makes the remaining moisture content 5 to 10 mass % in a viable cell cake produced under the same conditions as in actual production. However, the method is not particularly limited, and any method may be used, provided that it is rational.

After drying, the lyophilized composition is packed in a predetermined container, either directly or, as desired, after being processed such as by pulverization, and stored in places such as a cool, dark place at room temperature, or in a refrigerator or a freezer before use. Here, lyophilized compositions of viable cells of more than one bacterial strain may be mixed and packed together, if necessary. The form of package is not particularly limited. However, preferably, the lyophilized composition is packed by using a sealable material, for example, such as an ampule, a vial, or an aluminum bag. Alternatively, the lyophilized composition may be formed into granular particles, and then coated with a coating material (e.g., sugars such as pectin, and proteins such as gelatin). Since the viable cell count of *Rhizobium* bacteria contained in the present lyophilized composition hardly decreases with time when stored under refrigerated conditions in a temperature range of 0 to 10° C., for example at 5° C., the present lyophilized composition enables to be stored for years.

For its production, the present lyophilized composition requires an airtight container or airtight chamber that can withstand reduced pressure, a heater for complementing the heat lost by sublimation of ice, a cold trap for evacuating and capturing vapors from an airtight chamber, and a vacuum pump for creating a reduced pressure state, or a lyophilizer equipped with all of these units as a package. However, once produced, the lyophilized composition is very easy to store, and the cost of storage is minimal. Presently, a glycerol stock represents a common means of storing viable cells of microorganisms. However, this technique requires a high-performance freezer, such as a deep freezer that can accommodate a low-temperature setting as low as, for example, about −80° C. Because the very purpose of glycerol stock is storage, storage of viable cells of microorganisms, with no clear end point set for storage time, assumes that a high-performance freezer is able to keep consuming a large quantity of electric power almost endlessly, and that the power supply is stable and continuous. However, this assumption rarely holds in regions with unstable power supply such as in developing countries. The situation is not much different in developed countries, where a power supply could easily fail in the event of an unexpected power outage, and a standby power supply such as a generator is necessary as a backup measure against power failures. The present lyophilized composition can be stored for extended time periods with ordinary refrigerators as simple as those used in homes, and can remain sufficiently stable even when stored at ordinary temperature for as long as several months. Accordingly, no specific measures need to be taken for possible long blackouts of several hours to several days, providing a storage method for viable cells of *Rhizobium* bacteria without the need for a high-performance freezer, and a standby power supply or other peripheral equipment for keeping the freezer in operation.

When the *Rhizobium* bacteria used in the present invention are non-pathogenic, the present lyophilized composition can be used as an agrochemical composition. The agrochemical composition may be put to use in the as-produced form with the intention to be diluted with water at the actual site of crop production, or may be processed into a wettable powder or a powder form after being pulverized with a known pulverizer such as an impact pulverizer, and optionally mixed with, for example, a surfactant, a solid support, or other such adjuvants commonly used for agrochemical compositions.

The agrochemical composition of the present invention can be used to control crown gall disease and improve seed germination in agricultural and horticultural crops by being applied to plants (including the seeds) or soil. As used herein, the term "control" means preventing the plant of interest from infection with crown gall bacteria so as to avoid crown gall disease and tumor formation in the plant.

The agrochemical composition can exhibit marked effect in control of a crown gall disease caused in plants by tumor-forming, pathogenic crown gall bacteria. The types of plants to which the agrochemical composition is applicable are not particularly limited. Specific examples include Rosaceae plants such as apples, roses, Japanese plum, and cherries; Asteraceae plants such as *Chrysanthemum morifolium*; Vitaceae plants such as grapes; and Solanaceae plants such as tomatoes. The ARK-1 and ARK-3 strains exhibit a high crown gall disease control effect for all of these plants. The ARK-2 strain exhibits a crown gall disease control effect particularly for roses, grapes, and tomatoes. The K84 strain exhibits a crown gall disease control effect particularly for apples, roses, and chrysanthemums, for example *Chrysanthemum morifolium*.

The agrochemical composition of the present invention can be applied in a way that depends on the crop, and the mode of application may be appropriately selected according to the form of the agrochemical composition. For example, the agrochemical composition may be applied by spraying to a soil surface, soil injection, dipping a plant in bacterial solution, or dressing of a plant with a bacterial powder.

When using the agrochemical composition of the present invention as a suspension of viable cells of non-pathogenic *Rhizobium* bacteria by being added and dispersed in water, the concentration of viable cells of non-pathogenic *Rhizobium* bacteria in the suspension is not particularly limited, as long as it produces the desired control result. However, the concentration may be appropriately adjusted in a range of, for example, $10^7$ to $10^9$ cfu/mL because sufficient results may not be obtained when the concentration is too low, and the cells may be wasted when the concentration is too high.

When the agrochemical composition is used by being directly brought into contact with a plant in the form of a powder containing viable cells of non-pathogenic *Rhizobium* bacteria and pulverized particles of the present lyophilized composition, the concentration of viable cells of non-pathogenic *Rhizobium* bacteria in the powder is not particularly limited either. For example, the concentration may be appropriately adjusted in a range of $10^7$ to $10^9$ cfu/g.

There is no specific dose for the agrichemical composition of the present invention because the dose depends on conditions such as the crop, and the form of agrichemical composition. For example, in the case of soil injection where the agrichemical composition is applied in the form of a suspension after being added and dispersed in water, the dose for fruits such as grapes and apples may be 1 to 200 L per tree, depending on the tree size, and the agrichemical composition is preferably applied to parts of the soil to be planted with the plant, or at the base of the planted tree. In the case of immersion where a plant is immersed in a suspension of the agrichemical composition added and dispersed in water, for example, the root of the tree to be planted may be immersed for 10 minutes to 24 hours, or for 10 to 60 minutes in the case of seedlings of smaller grass plants, in the suspension prepared in a volume large enough to soak the root, though the method is not particularly limited. In the case where the agrichemical composition is directly brought into contact with a plant after being formulated into a powder form of dressing, for example, the root of the tree may be dust coated with the powder before planting, though the method is not particularly limited. When the plant of interest is a seed, the seed may be soaked with the suspension for 10 to 120 minutes, or may be dust coated, namely carried out dressing, by being mixed with the powder. It is also possible to spray the suspension over the seed surfaces after sowing the seeds in soil (soil injection).

As described above, a composition containing viable cells of *Rhizobium* bacteria and more than 10 mass % moisture is lyophilized to bring the moisture content to 10 mass %, and the drying is ended before the moisture content falls below 5 mass % so that the composition after the lyophilization contains the viable bacteria and 5 to 10 mass % moisture. In this way, the lyophilized composition containing viable cells of *Rhizobium* bacteria can have high viable cell viability, and the viable cells of *Rhizobium* bacteria in the lyophilized composition can remain viable during storage at 0 to 10° C., enabling stable and long storage.

EXAMPLES

Examples of the present invention are described below. It is to be noted that the present invention is not limited to the Examples below, and various modifications are possible within the technical idea of the present invention. In the following Examples, all procedures were aseptically performed. In the following, "part(s)" means part(s) by mass.

Test Example 1: Viable Cell Viability Immediately after Lyophilization

Preparation of NA (Nutrient Agar) Plate Medium

For preparation of NA plate medium, 5 parts of meat extract, 10 parts of peptone, 5 parts of sodium chloride, 15 parts of agar, and 1,000 parts of water were mixed, and heated to completely dissolve. The mixture was poured into a Petri dish, and cooled to prepare an NA plate medium.

Preparation of Preculture Medium

For preparation of preculture medium, 17 parts of soybean peptide, 3 parts of yeast extract, 2.5 parts of glucose, 5 parts of sodium chloride, and 1,000 parts of water were mixed.

Preparation of Main Culture Medium

A main culture medium was prepared in the same manner as in the preparation of preculture medium, except that 20 parts of maltose was used instead of 2.5 parts of glucose, and that 5 parts of polyoxyalkylene glycol was added as a defoaming agent.

Preparation of Aqueous Solution of Protecting Agent

In order to prepare an aqueous solution of a protecting agent, 20 parts of trehalose, 10 parts of sodium glutamate, parts of cysteine hydrochloride, 1 part of sodium carboxymethyl cellulose, and 61 parts of water were mixed, and the pH was adjusted to 7 with a small quantity of sodium hydroxide aqueous solution.

Preparation of Liquid Stock of Viable Cells

A glycerol stock of *Rhizobium vitis* ARK-1 strain was thawed, and inoculated to the NA plate medium. The cells were statically cultured at 28° C. for 1 day. One platinum loop (Öse) of the colonies formed was then transferred to inoculate the preculture medium, and the cells were grown by stirring culture for 26 hours. The aqueous culture solution was inoculated to the main culture medium, and the cells were grown by stirring culture at 28° C. for 43 hours. After main culture, the aqueous culture solution was centrifuged, and a viable cell concentrate of *Rhizobium vitis* ARK-1 strain was obtained by discarding the supernatant. After mixing 50 parts of the concentrate with 50 parts of the aqueous solution of a protecting agent, a small quantity of a sodium hydroxide aqueous solution was dropped to bring the pH to 7 and obtain a liquid stock of viable bacteria. The concentration of viable cells of *Rhizobium vitis* ARK-1 strain in the liquid stock of viable bacteria was $3.6 \times 10^{11}$ cfu/mL as measured by dilution plating method with the NA plate medium.

Preparation of Lyophilized Composition

Example 1

Twenty-five grams of the liquid stock of viable bacteria was transferred to a 100-mL eggplant flask. After prefreezing with a deep freezer set at −80° C., a lyophilized composition was obtained by lyophilizing the bacteria for 15 hours under a reduced pressure of about 5 to 10 Pa created in the eggplant flask, using a lyophilizer (Model FDU-2100, available from Tokyo Rikakikai Co., Ltd.). The lyophilized composition in the eggplant flask had a total mass of 8.1 g with a moisture content of 6.3 mass %.

Comparative Example 1

A lyophilized composition was obtained in the same manner as in Example 1, except that lyophilization was carried out for 6 hours. The lyophilized composition in the eggplant flask had a total mass of 11.6 g with a moisture content of 25.9 mass %. The lyophilized composition had stickiness.

Comparative Example 2

A lyophilized composition was obtained in the same manner as in Example 1, except that lyophilization was carried out for 10 hours. The lyophilized composition in the eggplant flask had a total mass of 9.5 g with a moisture content of 14.8 mass %. The lyophilized composition had stickiness.

Comparative Example 3

A lyophilized composition was obtained in the same manner as in Example 1, except that lyophilization was carried out for 24 hours. The lyophilized composition in the eggplant flask had a total mass of 7.1 g with a moisture content of 1.5 mass %.

Comparative Example 4

A lyophilized composition was obtained in the same manner as in Example 1, except that lyophilization was carried out for 48 hours. The lyophilized composition in the eggplant flask had a total mass of 7.0 g with a moisture content of 0.6 mass %.

Evaluation of Viable Cell Viability after Lyophilization

The viable cell concentrations (cfu/g) of the *Rhizobium vitis* ARK-1 strain in the lyophilized compositions of Example 1 and Comparative Examples 1 to 4 were measured by dilution plating method using the NA plate medium. The value from each sample was multiplied by the total mass (g) of the lyophilized composition to determine the total viable cell count (cfu) of the *Rhizobium vitis* ARK-1 strain in the lyophilized composition. For calculation of the viable cell viability (%) of *Rhizobium vitis* ARK-1 strain after lyophilization, the measured total viable cell count was divided by the total viable cell count $9 \times 10^{12}$ cfu (=$3.6 \times 10^{11}$ cfu/g×25 g) of *Rhizobium vitis* ARK-1 strain in 25 g of the liquid stock of viable bacteria. The results are presented in Table 1.

TABLE 1

| Lyophilized composition | Moisture content (%) | Total mass (g) | Viable cell concentration (cfu/g) | Total viable cell count (cfu) | Viable cell viability (%) |
|---|---|---|---|---|---|
| Example 1 | 6.3 | 8.1 | $7.8 \times 10^{11}$ | $6.3 \times 10^{12}$ | 70 |
| Com. Ex. 1 | 25.9 | 11.6 | $3.4 \times 10^{11}$ | $3.9 \times 10^{12}$ | 43 |
| Com. Ex. 2 | 14.8 | 9.5 | $4.7 \times 10^{11}$ | $4.5 \times 10^{12}$ | 50 |
| Com. Ex. 3 | 1.5 | 7.1 | $7.0 \times 10^{11}$ | $5.0 \times 10^{12}$ | 56 |
| Com. Ex. 4 | 0.6 | 7.0 | $6.8 \times 10^{11}$ | $4.8 \times 10^{12}$ | 53 |

These results confirmed that the lyophilization of the liquid stock of viable cells of *Rhizobium* bacteria to reduce the moisture content of the composition to about 6 mass % can produce a lyophilized composition of viable cells of *Rhizobium* bacteria having a viable cell viability that is about 15 to 25% higher than that of the composition having a moisture content of 1.5 mass % or less, or of the composition having a moisture content of 15 mass % or more. Under the foregoing conditions, the preferred drying time was found to be about 13 to 17 hours for the production of the present lyophilized composition.

Test Example 2: Viable Cell Viability after Long Storage Preparation of Liquid Stock of Viable Bacteria A glycerol stock of *Rhizobium vitis* ARK-1 strain was thawed, and inoculated to the NA plate medium. The cells were statically cultured at 28° C. for 1 day. One platinum loop (Öse) of the colonies formed was then transferred to inoculate the preculture medium, and the cells were grown by stirring culture for 25 hours. The aqueous culture solution was inoculated to the main culture medium, and the cells were grown by stirring culture at 28° C. for 42 hours using a 30-L jar fermenter. After main culture, the aqueous culture solution was centrifuged, and a viable cell concentrate of *Rhizobium vitis* ARK-1 strain was obtained by discarding the supernatant. After mixing 50 parts of the concentrate with 50 parts of the aqueous solution of a protecting agent prepared in Test Example 1, a small quantity of a sodium hydroxide aqueous solution was dropped to bring the pH to 7 and obtain a liquid stock of viable bacteria. The concentration of viable cells of *Rhizobium vitis* ARK-1 strain in the liquid stock of viable bacteria was $3.5 \times 10^{11}$ cfu/mL as measured by dilution plating method with the NA plate medium.

Preparation of Lyophilized Composition

From the liquid stock of viable bacteria, 7.0 g thereof was transferred to a 10-mL vial, and the bacteria were pre-frozen with a deep freezer set at −80° C. The cells were lyophilized for 48 hours under a reduced pressure of about 200 mTorr to obtain a lyophilized composition, using a lyophilizer (VirTis 25L Genesis SQ Super ES-55, available from SP Industries, Inc.). The lyophilized composition in the vial had a total mass of 2.0 g with a moisture content of 7.0 mass %.

Evaluation of Viable Cell Viability after Storage

After sealing the vial, the lyophilized composition was statically stored in a 4° C. refrigerator or in a 28° C. constant-temperature room. After a predetermined storage period, the concentration (cfu/g) of viable cells of the *Rhizobium vitis* ARK-1 strain in the vial was measured by dilution plating method with the NA plate medium, and the measured value was multiplied by the total mass (g) of the lyophilized composition to determine the total viable cell count (cfu) of the *Rhizobium vitis* ARK-1 strain in the lyophilized composition. For calculation of the viable cell viability (%) of *Rhizobium vitis* ARK-1 strain after storage, the measured total viable cell count was divided by the total viable cell count $2.5 \times 10^{12}$ cfu (=$3.5 \times 10^{11}$ cfu/g×7 g) of *Rhizobium vitis* ARK-1 strain in 7.0 g of the liquid stock of viable bacteria. Table 2 shows the results for storage at 4° C. Table 3 shows the results for storage at 28° C.

Test Example 3: Relationship Between Moisture Content and Viable Cell Viability

The NA (Nutrient Agar) plate medium, preculture medium, and protecting agent aqueous solution were prepared in the same manner as in Test Example 1. The main culture medium was prepared as follows.

Preparation of Main Culture Medium

Main culture medium was prepared by mixing 102 parts of soybean peptide, 18 parts of yeast extract, 30 parts of sodium chloride, 120 parts of maltose, 30 parts of Disfoam NQH-7403 (defoaming agent), and 6,000 parts of water.

Preparation of Liquid Stock of Viable Bacteria

Glycerol stocks of the *Rhizobium vitis* ARK-1 strain, *Rhizobium vitis* ARK-2 strain, *Rhizobium vitis* ARK-3 strain, and *Agrobacterium radiobacter* K84 strain were thawed, and inoculated to the NA plate medium. The cells were statically cultured at 28° C. for 1 day. For preculture, one platinum loop of the inoculum was transferred to inoculate the preculture medium. Preculture was carried out in a 28° C. constant-temperature room for 1 day using a rotary shaker (190 rpm). For main culture, the preculture solution of each strain was inoculated, and the cells were grown at 28° C. for 2 days using a 10-L jar fermenter. For the *Rhizobium vitis* ARK-1, ARK-2, and ARK-3 strains, the cells were grown under the controlled pH of 7.0 or less by

TABLE 2

| Storage time | Moisture content (%) | Total mass (g) | Viable cell concentration (cfu/g) | Total viable cell count (cfu) | Viable cell viability (%) | Percentage relative to day 0* |
|---|---|---|---|---|---|---|
| Immediately after drying (Day 0) | 7.0 | 2.0 | $7.1 \times 10^{11}$ | $1.4 \times 10^{12}$ | 56 | 100 |
| Day 10 | 7.0 | 2.0 | $7.1 \times 10^{11}$ | $1.4 \times 10^{12}$ | 56 | 100 |
| Day 20 | 7.0 | 2.0 | $8.0 \times 10^{11}$ | $1.6 \times 10^{12}$ | 64 | 114 |
| Day 30 | 7.0 | 2.0 | $7.2 \times 10^{11}$ | $1.4 \times 10^{12}$ | 56 | 100 |
| Day 120 | 7.0 | 2.0 | $8.3 \times 10^{11}$ | $1.7 \times 10^{12}$ | 68 | 121 |
| Day 372 | 7.0 | 2.0 | $7.1 \times 10^{11}$ | $1.4 \times 10^{12}$ | 56 | 100 |
| Day 547 | 7.0 | 2.0 | $9.4 \times 10^{11}$ | $1.9 \times 10^{12}$ | 76 | 136 |

*Percentage relative to day 0 (%) = (Viable cell viability)/(Viable cell viability immediately after lyophilization) × 100

TABLE 3

| Storage time | Moisture content (%) | Total mass (g) | Viable cell concentration (cfu/g) | Total viable cell count (cfu) | Viable cell viability (%) | Percentage relative to day 0* |
|---|---|---|---|---|---|---|
| Immediately after drying (Day 0) | 7.0 | 2.0 | $7.1 \times 10^{11}$ | $1.4 \times 10^{12}$ | 56 | 100 |
| Day 10 | 7.0 | 2.0 | $4.3 \times 10^{11}$ | $8.6 \times 10^{11}$ | 34 | 61 |
| Day 20 | 7.0 | 2.0 | $4.6 \times 10^{11}$ | $9.2 \times 10^{11}$ | 37 | 66 |
| Day 30 | 7.0 | 2.0 | $4.7 \times 10^{11}$ | $9.4 \times 10^{11}$ | 38 | 67 |
| Day 120 | 7.0 | 2.0 | $3.1 \times 10^{11}$ | $6.2 \times 10^{11}$ | 25 | 44 |
| Day 372 | 7.0 | 2.0 | $4.0 \times 10^{11}$ | $8.0 \times 10^{11}$ | 32 | 57 |
| Day 547 | 7.0 | 2.0 | $3.0 \times 10^{11}$ | $6.0 \times 10^{11}$ | 24 | 43 |

*Percentage relative to day 0 (%) = (Viable cell viability)/(Viable cell viability immediately after lyophilization) × 100

As demonstrated by these results, the viability of viable cells in the lyophilized compositions of *Rhizobium* bacteria according to the present invention did not decrease even after being stored for a year and a half under refrigerated conditions at 4° C., and showed only about a 50-percent decrease even under severe storage conditions at 28° C., confirming that the compositions are preservable for extended time periods.

maintaining a culture pH of 7.0 or below with phosphoric acid throughout the course of main culture. For the *Agrobacterium radiobacter* K84 strain, the cells were grown under the controlled pH of 6.0 or less by maintaining a culture pH of 6.0 or below with phosphoric acid throughout the course of main culture. After main culture, the liquid culture was centrifuged, and a viable cell concentrate was obtained by discarding the supernatant. After mixing 50 parts of the concentrate with 50 parts of the aqueous solution of a protecting agent, a small quantity of a sodium hydroxide aqueous solution was dropped to bring the pH to 7 and obtain a liquid stock of viable bacteria. The concentration of viable cells in the liquid stock of viable bacteria was measured by using an ordinary method.

Preparation of Lyophilized Composition

For preparation of a lyophilized composition, 25 g of the liquid stock of viable bacteria of each strain was transferred to a 100-mL eggplant flask, and the bacteria were pre-frozen with a deep freezer set at −80° C. The cells were lyophilized for different time periods under a reduced pressure of about 5 to 10 Pa created in the eggplant flask, using a lyophilizer (Model FDU-2100, available from Tokyo Rikakikai Co., Ltd.).

Evaluation of Viable Cell Viability after Lyophilization

The viable cell concentration (cfu/g) of the bacterial strain in each lyophilized composition was measured by an ordinary method. The measured value was multiplied by the total mass (g) of the lyophilized composition to determine the total viable cell count (cfu) of the bacteria in the lyophilized composition. For calculation of the viable cell viability (%) of each bacterial strain after lyophilization, the measured total viable cell count was divided by the total viable cell count of the bacterial strain in 25 g of the liquid stock of viable bacteria.

Table 4 shows the total viable cell count per eggplant flask before lyophilization of the liquid stock of viable cells of each bacterial strain.

TABLE 4

| Strain | Total mass (g) | Viable cell concentration (cfu/g) | Total viable cell count (cfu) |
|---|---|---|---|
| ARK-1 strain | 25 | $4.4 \times 10^{11}$ | $1.1 \times 10^{13}$ |
| ARK-2 strain | 25 | $4.1 \times 10^{11}$ | $1.0 \times 10^{13}$ |
| ARK-3 strain | 25 | $6.7 \times 10^{11}$ | $1.7 \times 10^{13}$ |
| K-84 strain | 25 | $4.3 \times 10^{11}$ | $1.1 \times 10^{13}$ |

Table 5 shows the viable cell count and viability of the *Rhizobium vitis* ARK-1 strain after lyophilization.

TABLE 5

| Moisture content (%) | Total mass (g) | Viable cell concentration (cfu/g) | Total viable cell count (cfu) | Viable cell viability (%) |
|---|---|---|---|---|
| 12.1 | 8.0 | $8.6 \times 10^{11}$ | $6.9 \times 10^{12}$ | 63 |
| 9.2 | 7.8 | $1.1 \times 10^{12}$ | $8.6 \times 10^{12}$ | 78 |
| 6.5 | 7.6 | $1.0 \times 10^{12}$ | $7.6 \times 10^{12}$ | 69 |
| 3.7 | 7.4 | $9.4 \times 10^{11}$ | $7.0 \times 10^{12}$ | 64 |
| 0.9 | 7.1 | $8.9 \times 10^{11}$ | $6.3 \times 10^{12}$ | 57 |

Table 6 shows the viable cell count and viability of the *Rhizobium vitis* ARK-2 strain after lyophilization.

TABLE 6

| Moisture content (%) | Total mass (g) | Viable cell concentration (cfu/g) | Total viable cell count (cfu) | Viable cell viability (%) |
|---|---|---|---|---|
| 15.4 | 8.2 | $8.7 \times 10^{11}$ | $7.1 \times 10^{12}$ | 71 |
| 9.7 | 7.6 | $1.0 \times 10^{12}$ | $7.6 \times 10^{12}$ | 76 |
| 5.6 | 7.5 | $1.0 \times 10^{12}$ | $7.5 \times 10^{12}$ | 75 |
| 4.5 | 7.4 | $9.5 \times 10^{11}$ | $7.0 \times 10^{12}$ | 70 |
| 1.8 | 7.2 | $9.4 \times 10^{11}$ | $6.8 \times 10^{12}$ | 68 |

Table 7 shows the viable cell count and viability of the *Rhizobium vitis* ARK-3 strain after lyophilization.

TABLE 7

| Moisture content (%) | Total mass (g) | Viable cell concentration (cfu/g) | Total viable cell count (cfu) | Viable cell viability (%) |
|---|---|---|---|---|
| 14.8 | 7.6 | $1.0 \times 10^{12}$ | $7.6 \times 10^{12}$ | 45 |
| 9.1 | 7.2 | $1.1 \times 10^{12}$ | $7.9 \times 10^{12}$ | 46 |
| 6.8 | 7.0 | $1.1 \times 10^{12}$ | $7.7 \times 10^{12}$ | 45 |
| 4.2 | 6.8 | $1.0 \times 10^{12}$ | $6.8 \times 10^{12}$ | 40 |
| 1.4 | 6.7 | $8.9 \times 10^{11}$ | $6.0 \times 10^{12}$ | 35 |

Table 8 shows the viable cell count and viability of the *Agrobacterium radiobacter* K84 strain after lyophilization.

TABLE 8

| Moisture content (%) | Total mass (g) | Viable cell concentration (cfu/g) | Total viable cell count (cfu) | Viable cell viability (%) |
|---|---|---|---|---|
| 14.9 | 7.2 | $9.2 \times 10^{11}$ | $6.6 \times 10^{12}$ | 60 |
| 9.8 | 7.1 | $1.1 \times 10^{12}$ | $7.8 \times 10^{12}$ | 71 |
| 5.9 | 6.5 | $1.2 \times 10^{12}$ | $7.8 \times 10^{12}$ | 71 |
| 3.1 | 6.3 | $1.2 \times 10^{12}$ | $7.6 \times 10^{12}$ | 69 |
| 0.6 | 6.1 | $9.7 \times 10^{11}$ | $5.9 \times 10^{12}$ | 54 |

The viable cell viability decreased with decrease of moisture content in all of the *Rhizobium vitis* ARK-1 strain, *Rhizobium vitis* ARK-2 strain, *Rhizobium vitis* ARK-3 strain, and *Agrobacterium radiobacter* K84 strain. In all probability, a high moisture content makes the lyophilized composition to more easily absorb moisture, and encourages mold growth. By using a lyophilized composition having a moisture content of 5 to 10 mass %, it is possible to stably obtain a preparation having high viable cell viability.

The present invention can be summarized as follows.

An objective of the present invention is to provide a method for producing a lyophilized composition of viable cells of *Rhizobium* bacteria having high viable cell viability, and a lyophilized composition of viable cells of *Rhizobium* bacteria having desirable long-storage survivability, among others.

The lyophilized composition of viable cells of *Rhizobium* bacteria having high viable cell viability and desirable long-storage survivability can be obtained when a composition containing viable cells of *Rhizobium* bacteria and more than 10 mass % moisture is lyophilized to bring the moisture content to 10 mass %, and the drying is ended before the moisture content falls below 5 mass % so that the composition after the lyophilization contains the viable bacteria and 5 to 10 mass % moisture.

REFERENCE TO DEPOSITED BIOLOGICAL MATERIAL

The deposition numbers of microorganisms that have been deposited in relation to the present invention are as follows.

(1) *Rhizobium vitis* ARK-1 strain (FERM BP-11426)
(2) *Rhizobium vitis* ARK-2 strain (FERM BP-11427)
(3) *Rhizobium vitis* ARK-3 strain (FERM BP-11428)

The invention claimed is:

1. A method for producing a lyophilized microbial composition comprising viable cells of a *Rhizobium* bacterium, the method comprising:

lyophilizing a composition comprising viable cells of a non-pathogenic *Rhizobium* bacterium, wherein the composition has a moisture content of more than 10 mass % moisture relative to a total mass of the composition, wherein the lyophilizing comprises freezing the composition and drying the composition under a reduced pressure to reduce the moisture content to 10 mass % relative to a total mass of the composition, ending the drying before the moisture content falls below 5 mass %, thus adjusting the moisture content of 5 to 10 mass % relative to a total mass of the lyophilized microbial composition, and obtaining a lyophilized microbial composition comprising viable cells of *Rhizobium* bacterium and having a moisture content of 5 to 10 mass %, wherein said composition has high viable cell viability and long-storage survivability compared to a microbial composition having less than 10 mass % of moisture relative to a total mass of the composition;

wherein the *Rhizobium* bacterium is at least one selected from the group consisting of *Rhizobium radiobacter, Rhizobium rhizogenes* and *Rhizobium vitis*.

2. The method of claim 1, wherein the *Rhizobium* bacterium is at least one selected from the group consisting of *Rhizobium vitis* ARK-1 strain (FERM BP-11426), *Rhizobium vitis* ARK-2 strain (FERM BP-11427), *Rhizobium vitis* ARK-3 strain (FERM BP-11428), and *Agrobacterium radiobacter* K84 strain.

3. A method of maintaining viability of *Rhizobium* cells, the method comprising:

lyophilizing a composition comprising viable cells of a non-pathogenic *Rhizobium* bacterium, wherein the composition has a moisture content of more than 10 mass % moisture relative to a total mass of the composition, wherein the lyophilizing comprises freezing the composition and drying the composition under a reduced pressure to reduce the moisture content to 10 mass % relative to a total mass of the composition, ending the drying before the moisture content falls below 5 mass %, thus adjusting the moisture content of 5 to 10 mass %, and obtaining a lyophilized microbial composition comprising viable cells of *Rhizobium* bacterium and having a moisture content of 5 to 10 mass %, wherein said composition has high viable cell viability and long-storage survivability compared to a microbial composition having less than 10 mass % of moisture relative to a total mass of the composition;

wherein the *Rhizobium* bacterium is at least one selected from the group consisting of *Rhizobium radiovacter, Rhizobium rhizogenes*, and *Rhizobium vitis*.

4. A method for controlling plant disease, the method comprising lyophilizing a composition comprising viable cells of a non-pathogenic *Rhizobium* bacterium, wherein the composition has a moisture content of more than 10 mass % moisture relative to a total mass of the composition, wherein the lyophilizing comprises freezing the composition and drying the composition under a reduced pressure to reduce the moisture content to 10 mass % relative to a total mass of the composition, ending the drying before the moisture content falls below 5 mass thus adjusting the moisture content of 5 to 10 mass %, obtaining a lyophilized microbial composition comprising viable cells of *Rhizobium* bacterium and having a moisture content 5 to 10 mass %, wherein said composition has high viable cell viability and long-storage survivability compared to a microbial composition having less than 10 mass % of moisture relative to a total mass of the composition, and applying the obtained composition to plant and/or soil; wherein the *Rhizobium* bacterium is at least one selected from the group consisting of *Rhizobium radiobacter, Rhizobium rhizogenes*, and *Rhizobium vitis*.

5. The method of claim 4, wherein the plant disease is crown gall disease.

6. The method of claim 4, wherein the *Rhizobium* bacterium is at least one selected from the group consisting of *Rhizobium vitis* ARK-1 strain (FERM BP-11426), *Rhizobium vitis* ARK-2 strain (FERM BP-11427), *Rhizobium vitis* ARK-3 strain (FERM BP-11428), and *Agrobacterium radiobacter* K84 strain.

7. The method of claim 3, wherein the *Rhizobium* bacterium is at least one selected from the group consisting of *Rhizobium vitis* ARK-1 strain (FERM BP-11426), *Rhizobium vitis* ARK-2 strain (FERM BP-11427), *Rhizobium vitis* ARK-3 strain (FERM BP-11428), and *Agrobacterium radiobacter* K84 strain.

\* \* \* \* \*